(12) United States Patent
Cassidy

(10) Patent No.: US 7,158,719 B2
(45) Date of Patent: Jan. 2, 2007

(54) MEDICAL FLUID WARMING SYSTEM (75) Inventor: David Cassidy, Chelmsford, MA (US)

(73) Assignee: Enginivity LLC, Lexington, MA (US)

( * ) Notice: Subject to any disclaimer, the term of this patent is extended or adjusted under 35 U.S.C. 154(b) by 324 days.

(21) Appl. No.: 10/876,824

(22) Filed: Jun. 25, 2004

(65) Prior Publication Data
US 2005/0008354 A1 Jan. 13, 2005

Related U.S. Application Data (60) Provisional application No. 60/485,929, filed on Jul. 9, 2003.

(51) Int. Cl.
F24H 1/10 (2006.01)
H05B 3/28 (2006.01)

(52) U.S. Cl. ........................ 392/494; 392/466

(58) Field of Classification Search ................ 392/494, 392/465, 466
See application file for complete search history.

(56) References Cited

U.S. PATENT DOCUMENTS

| 4,878,537 A | 11/1989 | Verkaart | 165/156 |
| 6,142,974 A | 11/2000 | Kistner et al. | 604/113 |
| 6,175,688 B1 | 1/2001 | Cassidy et al. | 392/470 |
| 6,236,809 B1 | 5/2001 | Cassidy et al. | 392/470 |
| 6,336,003 B1 | 1/2002 | Mitsunaga et al. | 392/470 |
| 6,535,689 B1 | 3/2003 | Augustine et al. | 392/470 |
| 6,554,791 B1 | 4/2003 | Cartledge et al. | 604/67 |

OTHER PUBLICATIONS

Orcus Inc., Thermal Management Solutions, 2002.
GrafTech International Ltd., Egraf 1200 Thermal Resistance vs. Pressure, 2002.
Estill Medical Technologies, Inc., Thermal Angel Blood and IV Fluid Infusion Warmer, Apr. 3, 2003.

*Primary Examiner*—Thor S. Campbell
(74) *Attorney, Agent, or Firm*—Weingarten, Schurgin, Gagnebin & Lebovici LLP (57) ABSTRACT

An improved inline intravenous fluid warming device. In one embodiment, the device includes a resistive film heater that is thermally coupled to a body having a serpentine fluid path extending therethrough. The film heater is coupled to the body via a first layer that is a thermally conductive and electrically insulative and a second layer that is thermally conductive. In another embodiment first and second resistive film heaters are employed to support either line power or battery powered operation.

48 Claims, 6 Drawing Sheets

MEDICAL FLUID WARMING SYSTEM

CROSS REFERENCE TO RELATED APPLICATIONS

The present application claims priority under 35 U.S.C. 119(e) of U.S. Provisional Patent Application titled MEDICAL FLUID WARMING SYSTEM, Application No. 60/485,929 filed Jul. 9, 2003.

STATEMENT REGARDING FEDERALLY SPONSORED RESEARCH OR DEVELOPMENT

N/A

BACKGROUND OF THE INVENTION

The present invention relates generally to an apparatus and method for infusing fluids into the body and more specifically to an inline fluid warmer.

It is understood that when introducing fluids to the body it is desirable to maintain the fluids generally at a temperature approximating the body temperature. It has been recognized that the introduction of fluids into the body at temperatures below the body temperature at high flow rates can induce hypothermia or shock. Additionally, it has been recognized that healing periods are increased in certain circumstances when fluids are introduced to the body that are below the body temperature.

Devices have been developed that are used to warm fluids prior to their infusion into the body. Two basic types of devices are used for warming fluids.

Bulk fluid warmers are known that warm the entire fluid volume to a specified temperature prior to the infusion. This type of fluid warmer requires that the warming process be initiated sufficiently in advance of the infusion to allow the fluid to be heated to the desired temperature. The requirement that the entire volume of fluid be warmed in advance of use makes this type of unit less desirable in certain applications, such as in emergency and trauma circumstances where the delay in infusing fluids could be potentially harmful or life threatening to a patient. Additionally, bulk fluid warmers are typically large fixed units that are not readily portable. Thus, the use of these devices is generally relegated to a fixed location. Moreover, once the fluids are warmed in bulk, the warmed fluids are typically transferred to and hung on an IV pole and delivered through a standard IV line which is around six feet in length. At low flow rates, the warmed fluids that exit the fluid container cool while traversing the IV line to the patient. Additionally, bulk fluid warmers are not suitable for use with some fluids that degrade if they are heated in advance and held at an elevated temperature for a prolonged period.

Inline fluid warmers have also been developed in an attempt to overcome some of the problems associated with bulk fluid warmers. An inline fluid warmer is a device that warms the fluid to be infused in the delivery line between the fluid source and the point of infusion into the body. Two general classes of inline fluid warmers are known.

One class of inline fluid warmers warms the fluids in the delivery line itself as the fluid passes through the delivery line. Such devices tend to be usable only at low flow rates since intravenous (IV) tubes are typically poor thermal conductors and it is difficult to efficiently transfer heat to a fluid passing through conventional IV tubes.

Another class of inline medical fluid warmers is interposed in the IV line set between the fluid source and the patient. Such devices warm the fluid to a desired temperature within the warming unit as the fluid passes through it. Such devices are more suitable for portable or field application and may be provided with a short output delivery tube to minimize the temperature drop in the fluid between the output of the inline fluid warmer and the infusion site. Such devices are also capable of use at high flow rates. Examples of these types of devices are disclosed in U.S. Pat. Nos. 6,142,974, 6,175,688, 6,336,003 6,236,809.

It would therefore be desirable to have an improved medical fluid warmer of small size that could be used either in operating room, clinical or field environments. It would further be desirable for the device to be cost effective to manufacture to promote the wide deployment and use of the device.

BRIEF SUMMARY OF THE INVENTION

In accordance with the present invention, an improved inline medical fluid warmer is disclosed. The fluid warmer includes a disposable body having input and output ports. A serpentine fluid path extends through the body between the input and output ports. The body is fabricated of a thermally conductive material and the fluid path is configured within the body to provide a large surface area that is in contact with the fluid.

An electrically powered resistive film heater is employed to heat the body. A phase transition material layer confronts the resistive film heater and a thermally conductive layer, such as graphite, is disposed in thermally conducting relation between the phase transition material layer and the body. The resistive film heater comprises a resistive film on an electrically insulative but thermally conductive substrate. A resistive film heater may be disposed on one or both sides of the body.

At least one first temperature sensor is disposed on the resistive film heater and senses the temperature of the body through substrate, the phase transition material layer and the thermally conductive graphite layer. At least one second temperature sensor is disposed on the resistive film heater on the opposite side of the heater from a portion of the resistive film and senses the temperature of the heater. In one embodiment, a pair of sensors are employed to sense the temperature of the body and the heater in the input end of the inline fluid warming device and a pair of sensors are employed to sense the temperature of the body and the heater at the output end of the fluid warming device. The sensor outputs are coupled to a controller that controls the power applied to the heater.

Other features, aspects and advantages of the presently disclosed medical fluid warmer will be apparent from the detailed description of the invention that follows.

BRIEF DESCRIPTION OF THE SEVERAL VIEWS OF THE DRAWINGS

The invention will be more fully understood by reference to the detailed description of the invention in conjunction with the drawings of which.

DETAILED DESCRIPTION OF THE INVENTION

U.S. Provisional Patent Application No. 60/485,929 titled MEDICAL FLUID WARMING SYSTEM filed Jul. 9, 2003 is hereby incorporated by reference.

In accordance with the present invention, an inline medical fluid warming device is disclosed. The disclosed inline fluid warming device may be fabricated so as to be sufficiently small to be positioned close to the patient, i.e. within inches of the infusion site. Additionally, since the warming device may be quite small, it may be strapped or otherwise affixed to the wrist or another body site of the patient.

Figure 1:
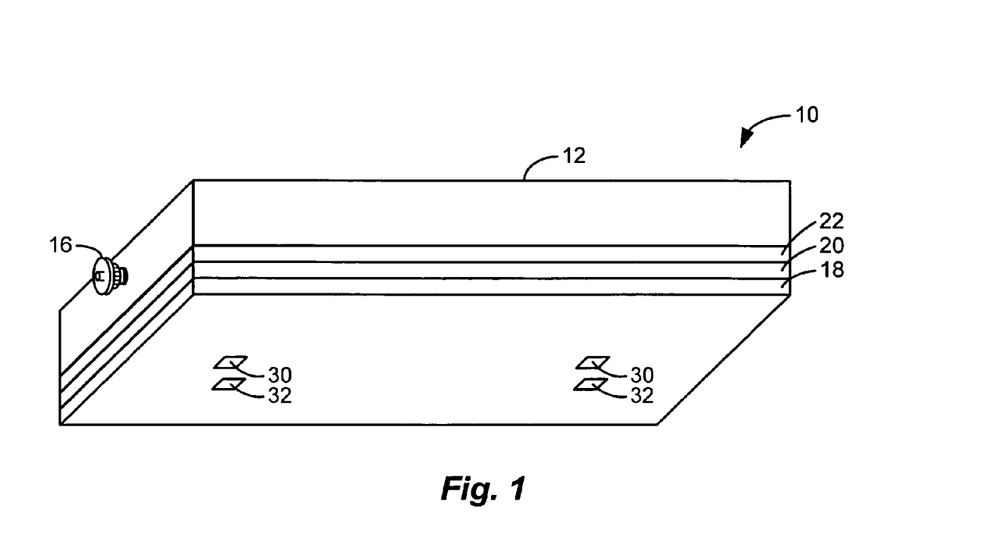
FIG. 1 is a perspective schematic view of an inline fluid warmer in accordance with the present invention.
Figure 2:
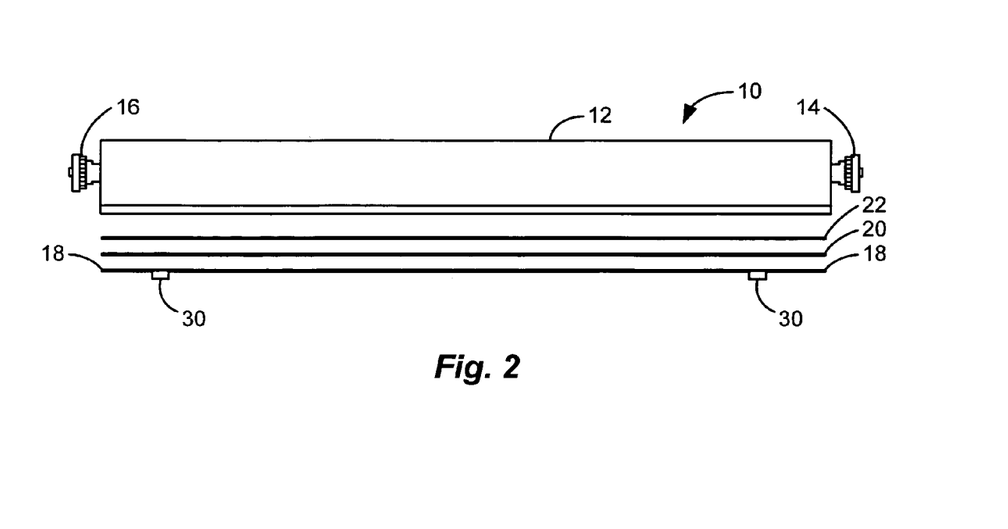
FIG. 2 is an exploded side view of the inline fluid warmer of FIG. 1.

Referring to FIGS. 1 and 2, the fluid warming device 10 has connectors 14, 16 at input and output ports respectively of a body 12 for connecting fluid delivery lines, such as intravenous line sets to the fluid warming device 10. The connectors, 14, 16 may be mounted to the body 12 or formed as an integral part of the body components. The body 12 includes a serpentine fluid path (see FIGS. 3d, 7a) that extends from the input port associated with the connector 14 to the output port associated with the connector 16. The body 12 serves as a heat exchanger that warms a fluid passing through the body 12. An electrically powered resistive film heater 18 is employed to heat the body 12 through first and second thermally conductive layers 20, 22 respectively. The resistive film heater 18 comprises a resistive film heater element that is deposited on an insulative substrate such as a polyimide film.

The resistance of the resistive film is specified based on the wattage desired and the voltage that is to be applied to the heater. To comply with certain regulatory specifications pertaining to safety, the DC voltage applied to the heater is maintained below 42 volts although it should be recognized that different voltages may be employed to drive the heater element and different resistances for the heater element may be employed to satisfy specific design objectives. For example, the heater element may have a resistance of between approximately 1.25 and 10 ohms when powered from a 42 volt source. In one embodiment, the resistance of the resistive heater element is approximately 6.4 ohms. In such embodiment, an AC to DC converter having a DC voltage output of approximately 36 volts powers the heater element. Wires from the AC to DC converter to the inline fluid warming device may be provided that are 18 gauge or greater to provide wire flexibility and to facilitate attachment of the fluid warming device to a wrist or another part of a patient's body.

The heater 18 has very low mass and stores very little thermal energy. The resistive film heater 18 includes first and second opposing surfaces. The second surface of the heater 18 faces the body 12 and confronts the thermally conductive layer 20. The resistive film is provided on the second surface of the insulative substrate. Although layer 20 is thermally conductive, it is an electrical insulator. The resistive film on the heater 18 is thus electrically insulated from the layer 22 which may comprise a conductive layer such as graphite.

The first layer 20 comprises a phase transition material in the form of a very thin, thermally conductive, electrically insulative film. The layer 20 is coated on both sides with a material that melts at approximately 52° C. The phase transition material in one embodiment is approximately 0.001" thick. The phase transition material layer 20 may comprise any suitable thermally conductive and electrically insulative interface layer. One such phase transition material is commercially available from Orcus, Inc., Overland Park, Kans. under the trade name THERMAPHASE ON KAPTON. The phase transition layer 20 bonds to both the second layer 22 and the resistive film heater 18 to produce a thermally conductive laminated structure.

The second layer 22 comprises a thermally conductive material such as graphite that is used to conduct heat passing through the phase transition material layer 20 to the body 12 of the device 10. The graphite layer 22 is typically between about 0.005" and about 0.015" thick. The melting of the coating on the phase transition material surfaces removes any air in tiny crevices in the graphite layer 22 and the resistive film heater 18 to which the phase transition layer 20 is thermally coupled. The second layer 22 may comprise any suitable thermally conductive material that provides a good thermal interface with the body 12 while being readily releasable from the body 12 to permit replacement of the body 12 following use. Thermal interface material sold under the trade name eGRAF1200 by Graftech International Ltd., Wilmington, Del. or EZT Foil 52 which is commercially available from Orcus, Inc. may be employed for the second layer 22.

The body 12 is urged into contact with the second layer 22, however, the second layer 22 does not adhere to the body 12. Thus, following use, the body 12 may be removed from the warming device 10 and replaced with a new body 12 for subsequent use.

The second surface of the film heater 18, the surfaces of the layers 20 and 22, and the surface of the body 12 that abuts the thermally conductive layer 22 are generally planar to promote efficient thermal conduction between the respective layers (FIG. 2).

Figure 9A:
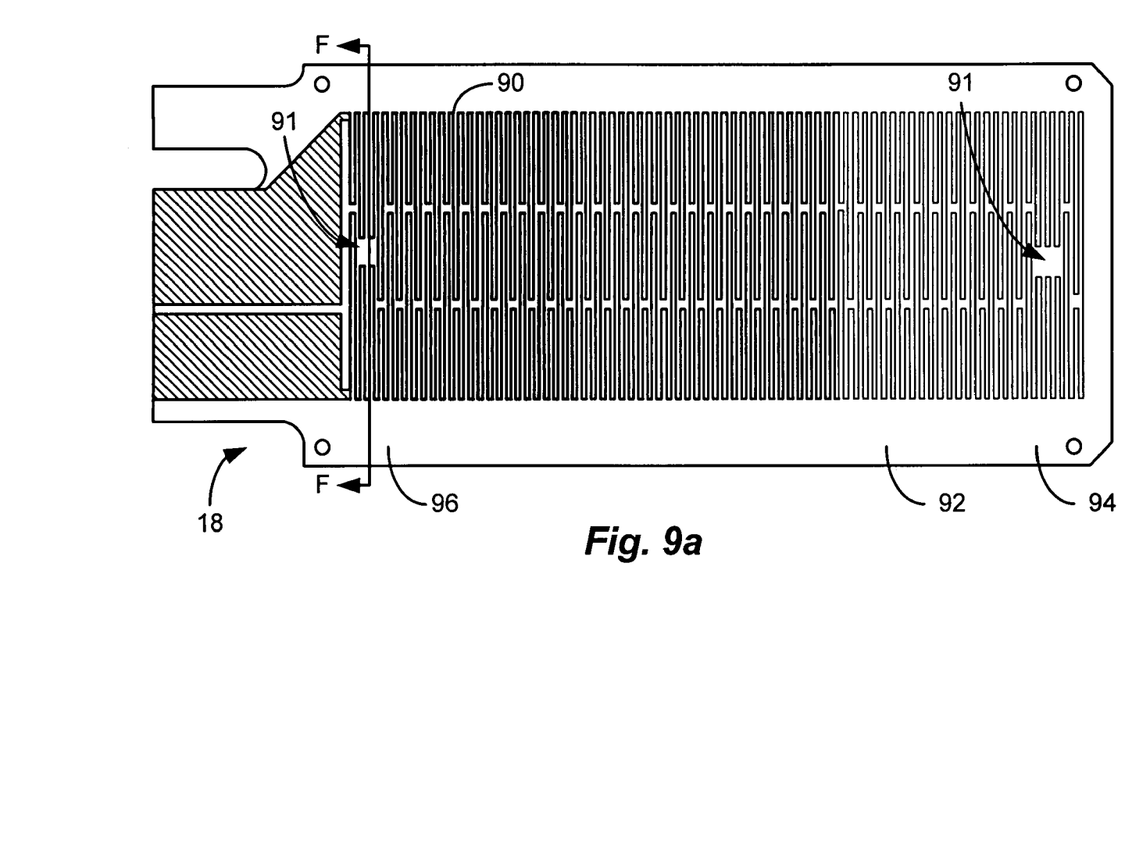
FIG. 9a is a top view of one embodiment of a resistive film heater for use in the embodiments depicted in FIGS. 2 and 6.
Figure 9B:
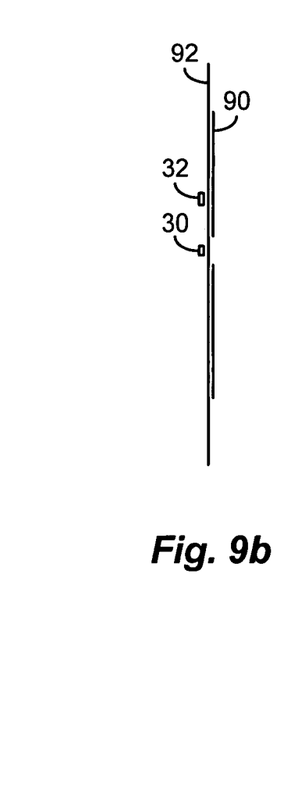
FIG. 9b is a cross-sectional view through the resistive film heater of FIG. 9a at section F—F.

First temperature sensors 30 are provided at the respective ends of the body and are mounted to the first surface of the substrate of the resistive film heater 18 (FIGS. 1, 9b). The first temperature sensors 30 may comprise thermistors or any other suitable temperature sensor. These sensors sense the temperature of the body 12 at their respective locations. The first temperature sensors 30 are mounted on the opposing surface of the insulative substrate of the resistive film heater 18 from the resistive film heater element and are located such that there is no portion of the resistive film heater element of the heater 18 is disposed between the sensors 30 and the body 12. Due to the thermally conductive nature of the phase transition layer 20 and the second layer 22, very accurate temperature measurements of the body 12 at the respective ends of the body 12 adjacent the input and output ports can be obtained using the sensors 30.

Second temperature sensors 32 are also mounted to the resistive film heater 18 and monitor the temperature of the heater 18 at the respective ends of the body 12. The second temperature sensors 32 may also comprises thermistors or any other suitable temperature sensors. The second temperature sensors 32 are used to monitor the temperature of the resistive film heater 18 at respective ends of the heater 18. The sensors 30, 32 are electrically coupled to a controller (subsequently discussed) and the power that is applied to the heater 18 is controlled based on the temperature indications from the sensors 30, 32 to prevent the film heater 18 from exceeding predetermined limits.

Figure 3A:
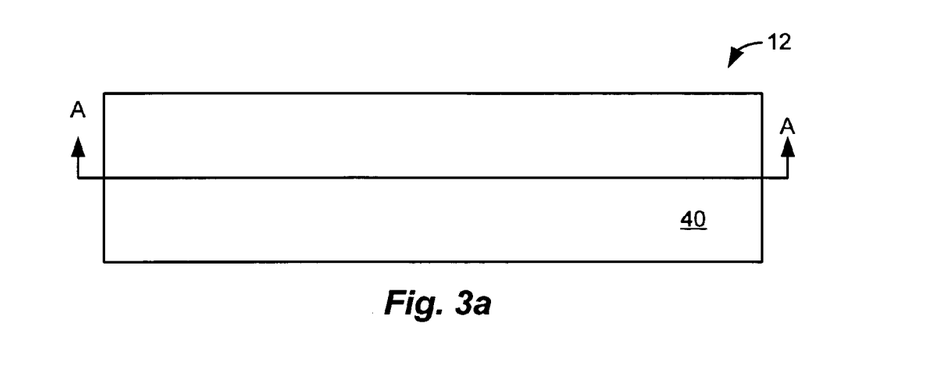
FIG. 3a is a top view of a first embodiment of a body for use in the presently disclosed medical fluid warmer.
Figure 3B:
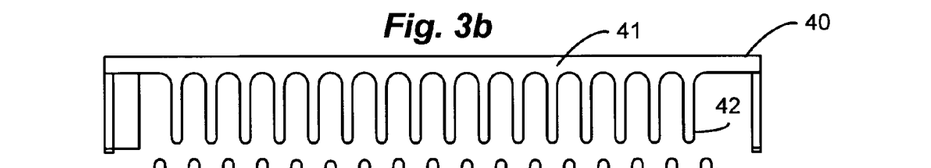
FIG. 3b is a side cross sectional view of a top portion of the body of FIG. 3a through section A—A.
Figure 3C:
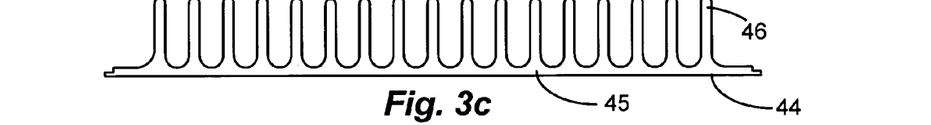
FIG. 3c is a side cross sectional view of a bottom portion of the body of FIG. 3a through section A—A.
Figure 3D:
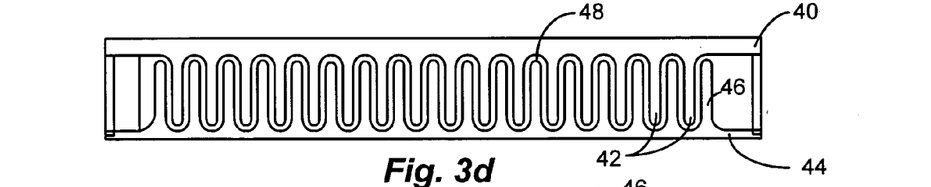
FIG. 3d is a side cross-sectional view of the body of FIG. 3a through section A—A.
Figure 3E:
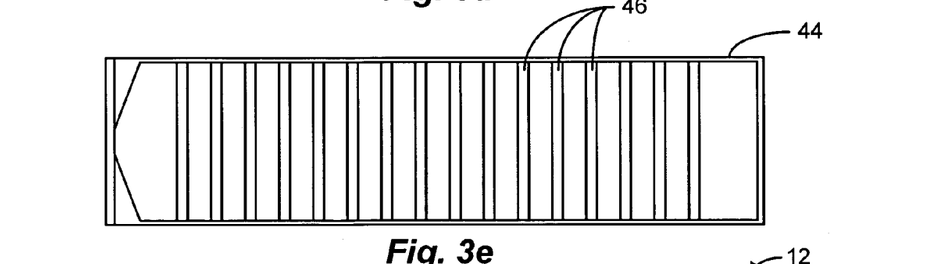
FIG. 3e is a bottom view of the top portion of the body depicted in FIG. 1b.
Figure 3F:
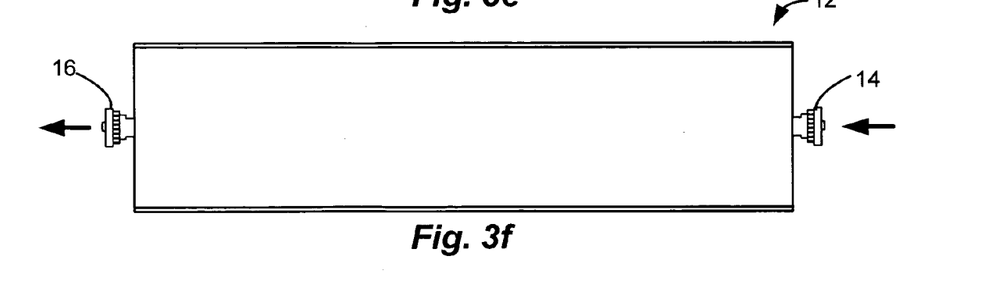
FIG. 3f is a bottom view of the body of the presently disclosed medical fluid warmer with input and output connectors mounted thereto.

FIGS. 3a–3f (collectively referred to as FIG. 3) depict one embodiment of the body 12 in greater detail. The body 12 includes a first portion 40 (FIG. 3b) and a second portion 44 (FIG. 3c) that are mateable. The first portion 40 includes a generally planar base section 41 and a plurality of integrally formed spaced fins 42 extending therefrom (FIG. 3b). The second portion 44 includes a generally planar base section 45 and a plurality of integrally formed spaced fins 46 extending from the base section 45 (FIG. 3c). The first and second portions 40 and 44 are mateable as depicted in FIG. 3d such that the fins 42 of the first portion 40 are disposed in the spaces between the fins 46 of the second portion 44 to define a serpentine path 48 extending through the body 12 (FIG. 3d). As illustrated in FIG. 3f, connectors 14 and 16 are mountable to the body 12 or alternatively are formed integrally with the body components to permit the connection of fluid lines to the fluid warming device 10.

The body 12 has an interior passage surface defining the fluid passage through the body 12. The surface area of the passage surface is significantly greater than the surface area of the surface confronting the conductive layer 22 or 68 as applicable. This relationship allows high heat transfer from the heater to the fluid but assists in assuring that significant electrical leakage currents are not coupled to the fluid.

The body 12 may be fabricated of any highly thermally conductive material such as aluminum, a thermally conductive plastic, a thermally conductive composite or any other suitable thermally conductive material that is, or can be made, biocompatible. For example, if a material is not biocompatible, it may be made biocompatible by the application of a biocompatible coating or plating.

Figure 4:
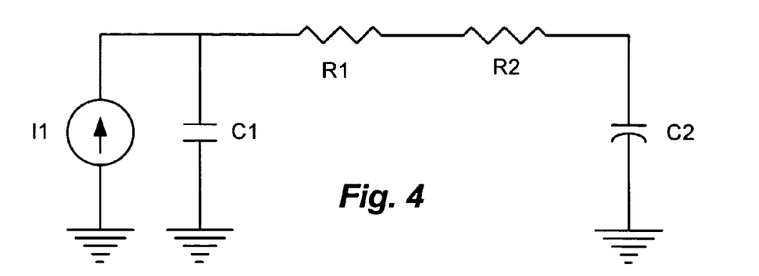
FIG. 4 is a simplified thermal diagram illustrative of the thermal configuration of the medical fluid warmer of FIG. 1.

FIG. 4 depicts a simplified thermal diagram that is illustrative of the fluid-warming device 10 in accordance with the present invention. The heater introduces power I1 in a heater mass C1. The heater 18 is of very low mass in comparison with the body 12 and consequently, is unable to store significant thermal energy. The phase transition material 20 has a low thermal resistance (designated R1) and the graphite material also has a low thermal resistance (designated R2). In one embodiment, the mass C2 of the body 12 and fluid passing through the body 12 collectively is at least 10 times greater than the mass C1 of the resistive film heater 18. Thus, the heater 18 can be run at a temperature that is considerably higher than the temperature of the body 12 without degrading the fluid passing through the body 12. The ability to run the heater at high temperatures allows more energy to be passed to the fluid in a smaller area. In the disclosed fluid warmer, if the fluid flow through the body 12 were to go instantly from a maximum flow rate to a zero flow rate, the resultant temperature rise of the fluid would be small since the energy stored at the resistive film heater 18 is small.

Figure 5:
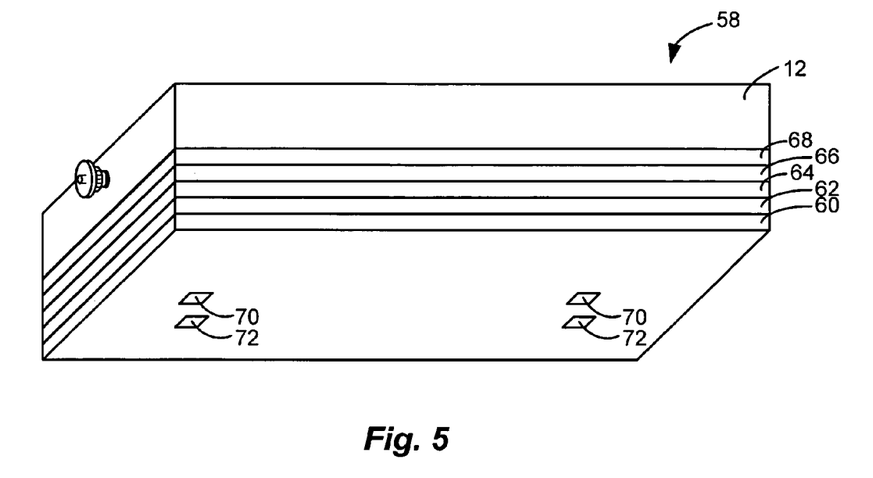
FIG. 5 is a schematic perspective view of a medical fluid warmer in accordance with the present invention that includes low voltage and high voltage heaters to support battery and line powered operation.
Figure 6:
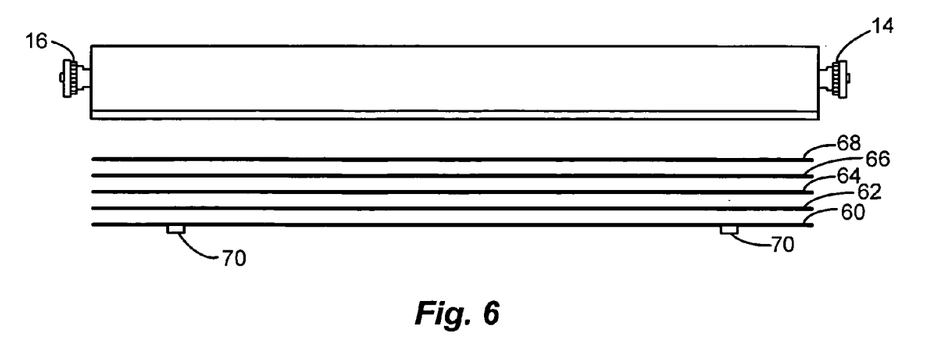
FIG. 6 is an exploded side view of the medical fluid warmer depicted in FIG. 5.

FIGS. 5 and 6 depict another embodiment of a medical fluid warmer 58 in accordance with the present invention. The fluid warmer 58 is fabricated as a laminated structure that includes a low voltage heater 64 for portable battery powered operation and a high voltage heater 60 for line powered operation.

More specifically, referring to FIGS. 5 and 6, the laminated structure includes a first resistive film heater 60 for line powered operation that is thermally coupled to a first phase transition material layer 62. The resistive film heater typically has a resistance of approximately 10 ohms or greater and is powered from the 115-volt line voltage. In one embodiment of the disclosed inline fluid warmer, the resistive film heater 60 has a resistance of 10 ohms. The resistance is specified so that the total wattage dissipated by the inline warming device will be 1440 watts or less pursuant to regulatory requirements. The resistance of the film heater is modified when the film heater is intended to be powered at 220 volts or some other voltage so that the device does not exceed the regulatory power limitation of the country of interest. The first phase transition material layer 62 is adhered to a low voltage film heater 64 that is configured for battery powered operation. The low voltage heater 64 also serves as a ground screen during line powered (AC) operation to prevent the coupling of leakage currents from the line-powered heater 60 to fluids in the body 12 of the fluid warmer 58. The low voltage heater 64 is an etched screen, such as a brass screen that is sandwiched between the phase transition material layers 62 and 66. The low voltage heater typically has a resistance of 0.012 ohms to 2 ohms to provide the necessary wattage. In one embodiment, the low voltage heater has a resistance of approximately 0.080 ohms and the device generates approximately 200 watts when the heater 64 is powered with a 4.2 volt battery. It should be recognized that the resistance of the heater and the battery voltage may be varied without departing from the concepts disclosed herein.

The surface of the phase transition material layer 66 on the opposite side from the low voltage heater 64 is adhered to a thermally conductive layer 68 which in one embodiment is a graphite layer. The graphite layer bonds to the phase transition material layer 66 and is urged into thermally conducting relation with a confronting surface of the body 12.

The thermally conductive layer 68 is readily removable from the body 12 to permit disposal and replacement of the body 12 following use. The laminated structure further includes two first temperature sensors 70 for sensing the temperature of the body 12 adjacent the input and output ports. The first temperature sensors 70 are mounted to the outer surface of the resistive film heater 60. The first temperature sensors 70 are mounted on the opposing surface of the insulative substrate of the resistive film heater 60 from the resistive film heater element and, are located such that there is no portion of the resistive film heater element of the heater 60 disposed between the sensors 70 and the body 12. Additionally, no portion of the heater 64 is disposed directly between the sensors 70 and the body 12. Thus, the sensors 70 sense the temperature of the body 12 and not the resistive film heater element of the heater 60 or the heater 64 when the heater 64 is the operative heater.

Additionally, the structure includes second temperature sensors 72 that are mounted to the outer surface of the substrate of the resistive film heater 60 at locations adjacent to opposite ends of the body 12. The resistive film that forms the heating element of the resistive film heater 60 is disposed on the opposite side of the insulative heater 60 substrate from the sensors 72. The sensors 72 are disposed over a portion of the resistive film forming the heating element and thus sense the temperature of the heating element when the line powered resistive film heater 60 is the operative heating element. When the low voltage heater 64 is employed for heating, the sensor 72 also senses the temperature of that heating element since the heating element of the lower voltage sensor 64 is disposed between the sensor 72 and the body 12. More specifically, since the second temperature sensors 72 are thermally coupled to the low voltage heater 64 through the first phase transition material layer 62, the second temperature sensors 72 may be employed to sense the temperature of either the line powered heater 60 or the low voltage heater 64.

The laminated stack-ups depicted in either FIG. 2 or FIG. 6 are urged against the disposable body 12 to maintain thermal contact with the body 12. For bodies having small surface areas (less than 4 sq. in.), the laminated stackup may be urged against the body using a spring to maintain the appropriate force. The force that is required to load the springs that are used with small area devices may generally be imparted by the human hand. In larger units in which the body 12 presents a larger surface area, air pressure may be employed to urge the body 12 into good thermal contact with the confronting graphite layer. The body 12 may be separated from the laminated stack-up by venting the air. A pressure of 5 PSI or greater provides suitable contact to achieve the desired thermal conductivity between the body 12 and the confronting graphite layer 68.

In the embodiments illustrated in FIGS. 1 and 2 and 5 and 6 respectively, the laminated structure is releasably urged against a single surface of the body 12. It should be appreciated that a similar laminated stackup may also be provided to confront the opposing side of the body 12 so that the body may be heated on opposing surfaces.

The layers 60, 62, 64, 66, 68 and the surface of the body 12 that abuts the thermally conductive layer 68 are generally planar to promote efficient thermal conduction between the respective layers (FIG. 6).

Figure 7A:
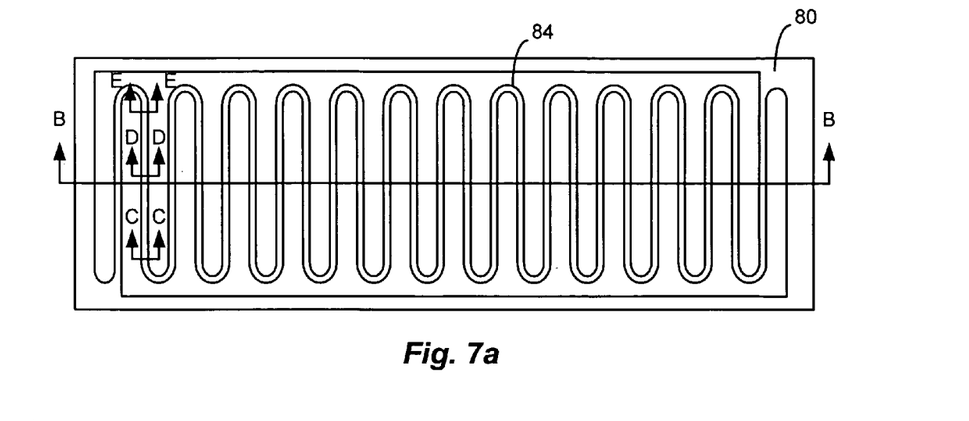
FIG. 7a is a top view of another embodiment of the bottom portion of a body for use in a medical fluid warmer in accordance with the present invention.
Figure 7B:
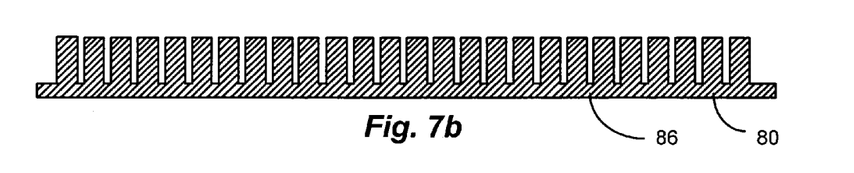
FIG. 7b is a side cross-sectional view of the bottom portion of the body of FIG. 7a through section B—B.
Figure 7C:
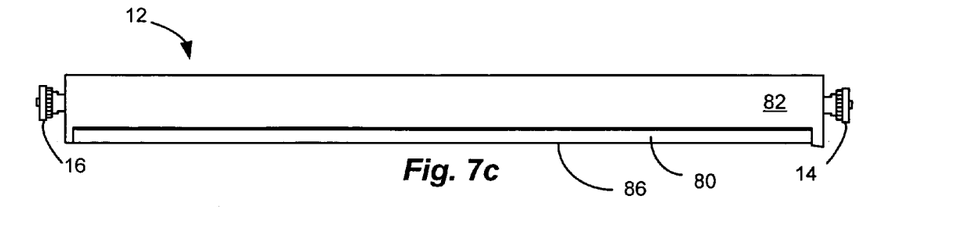
FIG. 7c is a side view of the bottom portion of the body of FIG. 7a with a top cover portion mounted thereto.

FIGS. 7a–7c (collectively FIG. 7) depict another embodiment of a body 12 for use in the fluid warming device depicted in FIGS. 1 and 2 or 5 and 6. This alternative embodiment of the body 12 includes a lower portion 80 and an upper portion or cover 82. The lower portion 80 includes a serpentine path 84 that extends through the lower portion 80 generally from one end of the lower portion 80 to the opposing end. The plane of the serpentine path 84 is generally parallel to the surface 86 of the lower portion 80 that is disposed in releasable thermally conductive relation with the applicable thermally conductive layer 22 (FIG. 2) or thermally conductive layer 68 (FIG. 6) depending upon the particular laminated stack-up employed.

FIG. 7b depicts a cross-section of the lower portion 80 of the body 12 through section BB of FIG. 7a. As illustrated in FIGS. 7a,b, the serpentine path 84 is defined between upstanding veins of the lower portion 80. The cover 82 is mountable to the lower portion 80 and provides a seal at the top of the lower portion 80 to cause the fluid to traverse the serpentine path 84 as it passes through the body 12.

The interior surface area of the body forming the fluid passage walls that contact the fluid passing through the body presently disclosed inline fluid warmer is greater than the surface area of the body that confronts the heater. In one embodiment having a alumium body, the surface area of the fluid passage walls is at least three times greater than the surface area of the heat transfer surface of the body 12 that confronts the laminated stackup containing the heater(s). In another embodiment having a thermally conductive plastic or composite body, the surface area of the fluid passage walls is at least two times greater than the surface area of the heat transfer surface of the body 12 that confronts the laminated stackup containing the heater(s).

Figure 8A:
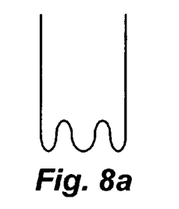
FIGS. 8a–8c are cross-sectional views through the bottom portion of the body depicted in FIG. 7a showing illustrative variations in the channel profile through sections C—C, D—D, and E—E respectively.
Figure 8B:
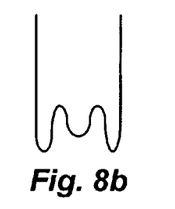
Figure 8C:
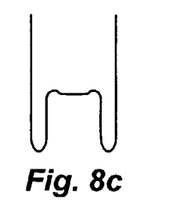

To promote mixing of the fluid as it passes through the body 12, the profile of the bottom of the channel forming the serpentine path 84 varies as depicted in FIGS. 8a–8c which correspond to cross-sectional views along sections CC, DD and EE in FIG. 7a. The variation in the bottom of the channel profile causes the fluid passing through the channel to be mixed so as to achieve a more uniform thermal gradient in the fluid passing through the fluid warmer 10. The variations in the bottom profile of the channel may be provided in some or all of the sections that form the serpentine path 84.

Figure 10:
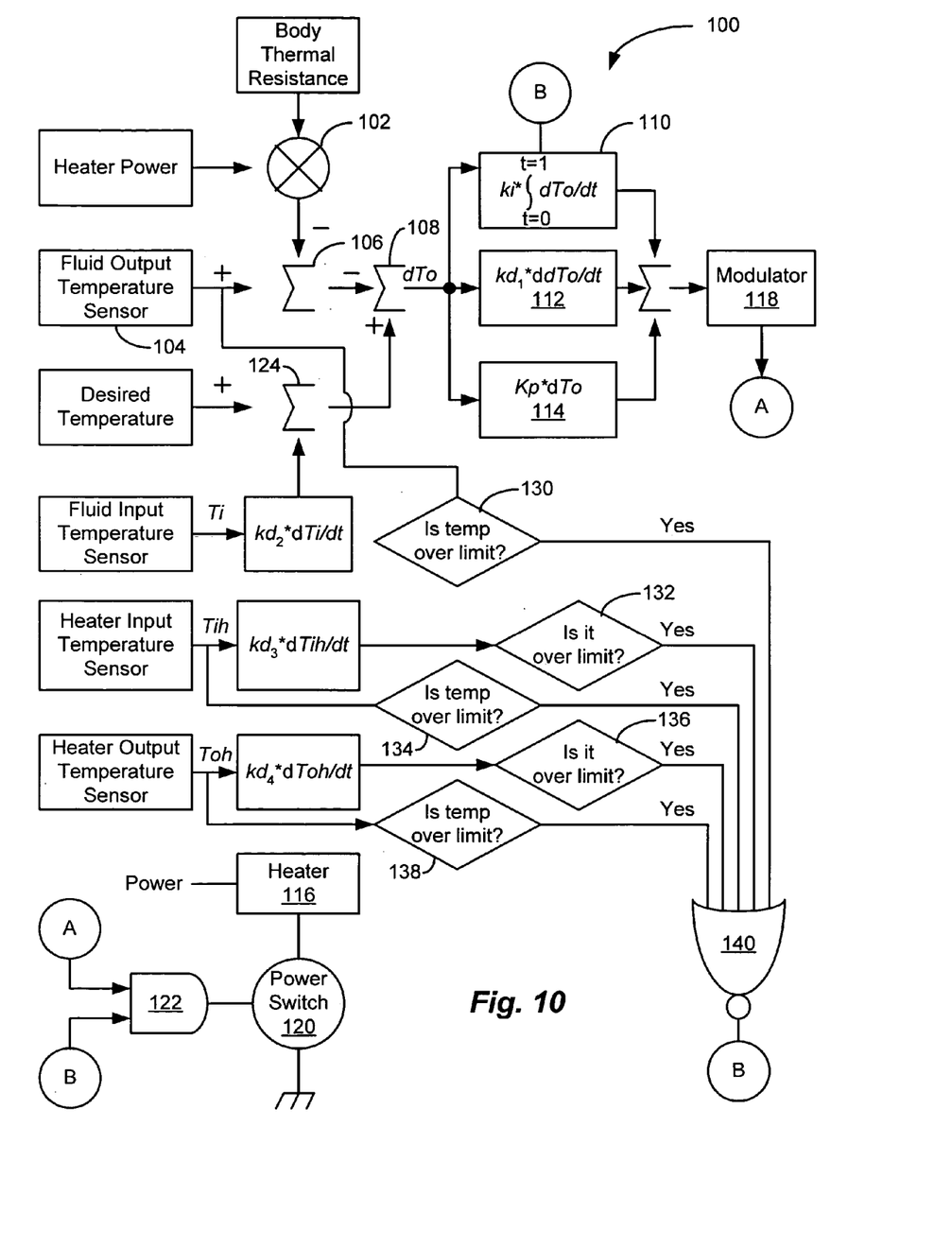
FIG. 10 is an illustrative block diagram of a device controller for powering a heater in the disclosed fluid warmer.

The fluid warming devices disclosed herein include a device controller that is responsive to the outputs of the temperature sensors at the input and output ends of the body and the flow rate of fluids passing through the fluid warming device to control the power applied to the operative heater. A block diagram illustrative of the operation of a device controller for use in the disclosed fluid warmer is shown in FIG. 10.

The device controller 100 includes a Proportional, Integral, Derivative (PID) controller. More specifically, the device 100 controller uses a multiplier 102 to calculate the product of the thermal resistance of the body 12 and the heater power. The device controller 100 detects the temperature at the output of the body 12 using a sensor 104 (corresponding to sensors 30, 70) and makes an adjustment for the thermal drop in the body 12 using a summer 106 that subtracts the product calculated using the multiplier 102 from the fluid output temperature obtained from the sensor 104. The resultant value at the output of the summer 106 is the calculated average fluid output temperature taking into account the thermal drop across the body 12. A temperature difference (dTo) is calculated using summer 108 by subtracting the calculated average fluid output temperature from the desired temperature. This temperature difference drives the PID controller comprising elements 110,112, 114.

The heater 116 is powered in a binary manner, i.e. it is either on or off. A modulator 118 is used to convert the analog output of the PID controller to a control signal "A" that drives a power switch 120 through AND gate 122. The derivative of the fluid input temperature is subtracted from the desired fluid temperature set point in summer 124. If the input fluid temperature begins to fall as measured using the fluid input sensor temperature sensor, more power is applied to the heater to increase the temperature of the fluid at the output of the body 12. More power is applied by increasing the duty cycle during which the heater element is powered. By increasing the power to the heater based on the fluid input temperature, one can assure that the fluid output temperature will not drop below a specified temperature threshold. If the input fluid temperature detected by the input fluid temperature sensor rises, the desired temperature that is input to the summer 124 will fall to keep from over heating the fluid. Monitoring and control circuitry comprising limit detectors and 130, 132, 134, 136, 138 and NOR gate 140 interrupts the signal from the modulator 118 and resets the PIDs' controller integral function if one of five potentially dangerous limits is exceeded.

The first limit is the output fluid temperature. If the limit detector 130 detects that the fluid output temperature sensor has exceeded 46 degrees C., the heater 116 is disabled.

The limit detectors 134 and 138 look at the actual heater temperatures at the input end of the body 12 and at the output end of the body 12 respectively. Additionally, the limit detectors 132 and 136 monitor the derivative of the heater temperatures at the input end and the output end of the body 12 to detect the removal of the body 12 from thermal contact with the heater 116. In the event any of the limit detectors 132, 134, 136 and 138 detect that a limit has been exceeded, the heater 116 is disabled.

The input pair of temperature sensors (body temperature and heater temperature sensors) or the output pair of temperature sensors can also be used to determine the heat flux entering the body 12. This is accomplished by taking the temperature difference and dividing by the thermal resistance of the heater. This calculation can be used instead of the electrical heater power calculation of current squared times ohms as the heater resistance does change with temperature.

It will be appreciated that greater power is applied by the device controller to the operative resistive film heater to achieve a desired fluid exit temperature at higher flow rates than is necessary to achieve the same desired fluid exit temperature at lower flow rates.

The fluid warming device may be line powered in which case the power for line powered resistive film heater and the power controller is derived from the line power. Alternatively, the fluid warming device may be battery powered in which case the power for the power controller and the low voltage resistive film heater is derived from the battery power. Moreover, using the laminated stack-up structure depicted in FIGS. 5 and 6, the single fluid warming device 58 may be either line powered or battery powered to provide flexibility in use.

The control elements for the device controller 100 may be implemented in hardware, software, firmware or a combination of hardware, firmware, and/or software. The block diagram of FIG. 10 is intended to illustrate exemplary functions being performed in the device controller 100.

While the embodiments depicted herein depict a single fluid path from one end of the fluid warming device to the opposing end, multiple fluid paths may be provided to further increase the surface area that the fluid contacts so as to promote efficient heat transfer from the interior surfaces of the body 12 along the serpentine paths.

An illustrative resistive film heater 18 for use with the presently disclosed medical warming device is depicted in FIG. 9. The illustrative heater is a low voltage heater having a conductive film deposited on a polyimide substrate. The resistance of the conductive path is approximately 6.4 ohms, although it is recognized that the resistance of the conductive path may vary based on the voltage to be applied and the desired wattage to be achieved. A resistive film heater element 90 is disposed along a serpentine path on an insulative substrate 92. The heater element 90 extends from a first end 94 of the substrate 92 that is adjacent the input port of the body 12 (FIG. 2), and a second end 96 of the substrate that is disposed adjacent the output port of the body 12 when the heater 18 is disposed in a mounting position with respect to the body 12. In one embodiment, the heater element 90 is configured such that the resistance of the heater element 90 per linear inch is greater adjacent the first end 94 than at the second end 96 of the heater 18. This is achieved by increasing the width of the heater element at discreet points between from the first end of the heater element 90 and the second end of the heater element 90. Although FIG. 9a depicts 3 changes in sections having different resistances per linear inch, a greater or lesser number of sections may be provided to achieve the desired heat profile. Alternatively, the change in the width of the resistive element 90 may be progressive rather than at discreet points along the path of the heater element 90. The contacts at the ends of the heater element 90 may both be provided at one end of the heater 18 as depicted in FIG. 9a or alternatively at opposing ends of the heater 18. More specifically, in the heater depicted in FIG. 9a, both ends of the resistive etch path are adjacent the second end of the heater. Thus, following the resistive path from the first contact at one end of the resistive path to the second contact at the second end of the resistive path, the resistance of the heater element 90 per linear inch increases progressively from the first contact as the path traverses the substrate toward the first end and decreases progressively as the heater element 90 traverses the substrate from the first end to the second contact. The changes in the resistance per linear inch occur at discreet points along the path of the heater element 90.

The first temperature sensors 30, 70 are mounted to the substrate 92 on the opposite side of the substrate 92 from the heater element 90 and in the area corresponding to the openings 91 in heater element 90. By positioning the sensors 30, 70 over the openings 91 in the heater element, the sensors 30, 70 sense the temperature of the body 12 rather than the heater element 90.

It will further be appreciated by those of ordinary skill in the art that modifications to and variations of the above described fluid warming device and methods for warming a fluid in an inline intravenous fluid warmer may be made without departing from the inventive concepts disclosed herein. Accordingly, the invention should not be viewed as limited except as by the scope and spirit of the appended claims.

What is claimed is:
1. A fluid warming device comprising:
a thermally conductive body having an input port and an output port, said body having a serpentine fluid passage extending through said body from said input port to said output port, said body including a first surface;
a first resistive film heater;
at least one thermally conductive layer thermally coupling said resistive film heater to said first surface of said body;
wherein said at least one thermally conductive layer includes a first phase transition material layer disposed in thermally conductive relation between said resistive film heater and said first surface of said body;
wherein said first phase transition material layer is electrically insulative;

wherein said at least one thermally conductive layer includes a second thermally conductive layer disposed in thermally conductive relation between said first phase transition material layer and said first surface of said body; and wherein said second layer is a graphite layer.

2. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive film heater to said first surface of said body; and wherein said body includes first and second body portions mated one to the other to form said body and wherein said serpentine fluid passage is formed between surfaces of said first and second body portions.

3. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive film heater to said first surface of said body; and wherein said first and second body portions each includes a base portion and a plurality of integrally formed spaced fins extending from the base portion, wherein said fins of each of said first and second body portions are disposed between the fins of the other one of said first and second body portions when the first body portion is mated to said second body portion and said serpentine path is formed between the fins of said first and second body portions.

4. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive turn heater to said first surface of said body; and wherein said body includes a first body portion having a channel that defines said serpentine path, wherein said first surface is generally planar and said channel is generally parallel to said first surface of said body, said body further including a second body portion that is mated with said first body portion as a cover that defines an upper wall of said channel.

5. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive film heater to said first surface of said body; and wherein said first resistive film heater includes an insulative substrate and a resistive heater element on one surface of said substrate, said fluid warming device further including at least one first temperature sensor in thermal communication with said substrate and coupled to the opposing surface of said substrate from said resistive heater element, said at least one first temperature sensor being operative to provide at least one indication of the temperature of said body.

6. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive film heater to said first surface of said body;

wherein said at least one thermally conductive layer includes a first phase transition material layer disposed in thermally conductive relation between said resistive film heater and said first surface of said body;

wherein said first phase transition material layer is electrically insulative;

wherein said at least one thermally conductive layer includes a second thermally conductive layer disposed in thermally conductive relation between said first phase transition material layer and said first surface of said body; and further including a second heater and a second phase transition material layer, said first and second heaters, said first and second phase transition material layers and said thermally conductive layer each having respective first and second opposing surfaces and collectively forming a laminated structure in which:

said second surface of said first heater is mated to a first surface of said first phase transition material layer, said second surface of said first phase transition material layer is mated to said first surface of said second heater;

said second surface of said second heater is mated to said first surface of said second phase transition material layer, said second surface of said second phase transition material layer is mated to said first surface of said thermally conductive layer, and said second surface of said thermally conductive layer is disposed in releasable abutting relation with said first surface of said body; and wherein said first resistive film heater is configured for line powered operation and said second heater is configured for operation at a voltage under ten volts.

7. A fluid warming device comprising:

a thermally conductive body having an input port and an output port, said body having a serpentine fluid passage extending through said body from said input port to said output port, said body including a first surface;

a first resistive film heater;

at least one thermally conductive layer thermally coupling said resistive film heater to said first surface of said body;

wherein said at least one thermally conductive layer includes a first phase transition material layer disposed in thermally conductive relation between said resistive film heater and said first surface of said body;

wherein said first phase transition material layer is electrically insulative;

wherein said at least one thermally conductive layer includes a second thermally conductive layer disposed in thermally conductive relation between said first phase transition material layer and said first surface of said body; and further including a second heater and a second phase transition material layer, said first and second heater, said first and second phase transition material layers and said thermally conductive layer each having respective first and second opposing surfaces and collectively forming a laminated structure in which:
said second surface of said first heater is mated to a first surface of said first phase transition material layer,
said second surface of said first phase transition material layer is mated to said first surface of said second heater,
said second surface of said second heater is mated to said first surface of said second phase transition material layer,
said second surface of said second phase transition material layer is mated to said first surface of said thermally conductive layer, and
said second surface of said thermally conductive layer is disposed in releasable abutting relation with said first surface of said body; and
wherein said first resistive film heater includes an insulative substrate and a resistive path disposed on one surface of said substrate, said fluid warming device further including a first temperature sensor in thermal communication with said substrate and coupled to the opposing surface of said substrate from said resistive path, said first temperature sensor being operative to provide an indication of the temperature of said body.

8. A fluid warming device comprising:
a thermally conductive body having an input port and an output port, said body having a serpentine fluid passage extending through said body from said input port to said output port, said body including a first surface;
a first resistive film heater;
at least one thermally conductive layer thermally coupling said resistive film heater to said first surface of said body; and
wherein said resistive film heater includes a heater element extending between a first end that is adjacent said input port of said body and a second end that is adjacent the output port of said body, wherein said heater element is configured such that the resistance of said etch per linear inch adjacent said first end is greater than the resistance of said etch per linear inch at said second end and the resistance of said etch decreases from said first end to said second end.

9. A heat exchanger for use in an inline fluid warming device comprising:
a thermally conductive body having an input port and an output port, said body having a serpentine fluid passage extending through said body between said input port and said output port, said body having at least one heat transfer surface for transferring heat from at least one heater to said body, said body including:
a first portion having a generally serpentine fluid path oriented generally parallel to said heat transfer surface; and
a second portion mated to said first portion, said second portion comprising a cover defining at least a portion of the walls of said fluid path.

10. A heat exchanger for use in an inline fluid warming device comprising:
a thermally conductive body having an input port and an output port, said body having a serpentine fluid passage extending through said body between said input port and said output port, said body having at least one heat transfer surface for transferring heat from at least one heater to said body,
wherein said fluid passage includes fluid passage walls of a first surface area and said at least one heat transfer surface has a second surface area and said first surface area is at least two times greater than said second surface area.

11. A heat exchanger for use in an inline fluid warming device comprising:
a thermally conductive body having an input port and an output port, said body having a serpentine fluid passage extending trough said body between said input port and said output port, said body having at least one heat transfer surface for transferring heat from at least one heater to said body, said body including first and second portions, said first portion having a first plurality of generally parallel fins integrally formed with and extending from a first base, said second portion having a second plurality of generally parallel fins integrally formed with and extending from a second base, said first portion being mated to said second portion such that said first plurality of fins are disposed between and spaced from said second plurality of fins to define said serpentine path between said first and second plurality of fins.

12. The fluid warming device of claims 2, 3, 4, 5, or 8, wherein said at least one thermally conductive layer includes a first phase transition material layer disposed in thermally conductive relation between said resistive film heater and said lint surface of said body.

13. The fluid warming device of claim 12 wherein said first phase transition material layer is electrically insulative.

14. The fluid warming device of claims 13 or 1, wherein said first phase transition material layer includes a coating on each side of the layer and wherein said coating has a melting point in the range of about 47–57 degrees centigrade.

15. The fluid warming device of claim 14 wherein said first phase transition material layer is approximately 0.001 inch thick.

16. The fluid warming device of claim 13 wherein said at least one thermally conductive layer includes a second thermally conductive layer disposed in thermally conductive relation between said first phase transition material layer and said first surface of said body.

17. The fluid warming device of claim 16 wherein said second layer is releasably mateable with said first surface of said body.

18. The fluid warming device of claim 1 wherein said graphite film has a thickness between approximately 0.05" and 015'.

19. The fluid warming device of claims 1, 2, 3, 4, 5, 6, 7, or 8, wherein said body comprises an aluminum body.

20. The fluid warming device of claims 1, 2, 3, 4, 5, 6, 7, or 8, wherein said body comprises a thermally conductive plastic.

21. The fluid warming device of claims 1, 2, 3, 4, 5, 6, 7, or 8, wherein said first resistive film heater includes a heater element having a resistance between 1.5 ohms and 10 obms.

22. The fluid warming device of claim 5 further including at least one second temperature sensor in thermal communication with said substrate and coupled to the opposing surface of said substrate from said resistive heater element, said at least one second temperature sensor being positioned to sense the temperature of said resistive heater element.

23. The fluid warming device of claim 22 wherein said at least one first sensor includes two first sensors mounted to said substrate adjacent first and second ends of said body and said at least one second sensor includes two second sensors mounted to said substrate adjacent said first and second ends of said body.

24. The fluid warming device of claim 23 further including a controller electrically coupled to said two first sensors and said two second sensors and receiving signals therefrom, said controller operative in response to the signals received from said to control the power applied to said first heater.

25. The fluid warming device of claim 16 further including a second heater and a second phase transition material layer, said first and second heaters, said first and second phase transition material layers and said thermally conductive layer each having respective first and second opposing surfaces and collectively forming a laminated structure in which:
said second surface of said first heater is mated to a first surface of said first phase transition material layer,
said second surface of said first phase transition material layer is mated to said first surface of said second heater,
said second surface of said second heater is mated to said first surface of said second phase transition material layer,
said second surface of said second phase transition material layer is mated to said first surface of said thermally conductive layer, and
said second surface of said thermally conductive layer is disposed in releasable abutting relation with said first surface of said body.

26. The fluid warming device of claim 6 wherein said second resistive film heater comprises a conductive screen that provides an electronic shield to reduce the coupling of AC fields to fluid passing through said warming device when said first resistive film heater is line powered.

27. The fluid warming device of claims 1, 2, 3, 4, 5, 6, 7, or 8, wherein said body includes walls defining said serpentine path and said walls have a non-uniform contour to promote mixing of fluid passing through said body.

28. The fluid warming device of claim 7 further including a second temperature sensor thermally coupled to said first resistive film heater, said second temperature sensor operative to provide an indication of the temperature of one of said first and second heaters.

29. The fluid warming device of claim 28 further including a power controller operative to control the power applied to one of said first and second heaters in response to outputs from said first and second temperature sensors to control the temperature of fluids exiting said body.

30. The fluid warming device of claims 1, 2, 3, 4, 5, 6, 7, or 8, wherein said first surface of said body, said first resistive film heater and said at least one thermally conductive layer are generally planar.

31. The fluid warming device claims 2, 3, 4, 5, 8, wherein said at least one thermally conductive layer includes an electrically insulative and thermally conductive first layer and a second thermally conductive layer, wherein said first layer is disposed between and in contact with said first heater and said second layer, and said second layer is disposed between and in thermally conductive relation with said first layer and said first surface of said thermally conductive body.

32. The fluid warming device of claim 8 wherein said resistance of said changes at discreet points between said first end and said second end.

33. The fluid warming device of claims 1, 2, 3, 4, 5, 6, 7, or 8, wherein said fluid passage is defined by interior surfaces of said body having an interior surface area, wherein said interior surface area is greater than the surface area of said first surface of said body.

34. The fluid warming device of claim 33 wherein said interior surface area is at least two times greater than the surface area of said first surface.

35. The fluid warming device of claims 1, 2, 3, 4, 5, 6, 7, or 8, wherein said body and fluid within said body have a first mass and said resistive film heater has a second mass and said first thermal mass is at least ten times greater than said second mass.

36. The fluid warming device of claims 1, 2, 3, 4, 5, 6, 7, or 8, wherein said resistive film heater comprises a flexible resistive film heater.

37. The heat exchanger of claim 9 wherein said at least one heat transfer surface is generally planar.

38. The heat exchanger of claim 9 wherein said body is aluminum.

39. The heat exchanger of claim 9 wherein said body is a thermally conductive plastic.

40. The heat exchanger of claim 9 wherein said body is a thermally conductive composite.

41. The heat exchanger of claim 11 wherein said body is a thermally conductive composite.

42. The heat exchanger of claim 9 wherein said first and second portions comprise the same material.

43. The heat exchanger of claim 10 wherein said body is aluminum.

44. The heat exchanger of claim 10 wherein said body is a thermally conductive plastic.

45. The heat exchanger of claim 10 wherein said body is a thermally conductive composite.

46. The beat exchanger of claim 11 wherein said body is aluminum.

47. The heat exchanger of claim 11 wherein said body is a thermally conductive plastic.

48. The heat exchanger of claim 11 wherein said first and second portions comprise the same material.

* * * * *

UNITED STATES PATENT AND TRADEMARK OFFICE
CERTIFICATE OF CORRECTION

PATENT NO. : 7,158,719 B2 Page 1 of 1
APPLICATION NO. : 10/876824
DATED : January 2, 2007
INVENTOR(S) : David Cassidy It is certified that error appears in the above-identified patent and that said Letters Patent is hereby corrected as shown below:

Column 11, claim 4, line 45, "turn heater" should read --film heater--;

Column 14, claim 11, line 13, "trough said body" should read --through said body--;

Column 14, claim 12, line 31, "lint surface" should read --first surface--;

Column 14, claim 18, lines 52-53 "between approximately 0.05" and 015'." should read --between approximately .005" and .015".--;

Column 14, claim 21, line 61 "obms." should read --ohms.--;

Column 16, claim 32, line 11, "said changes" should read --said etch changes--; and Column 16, claim 46, line 48, "beat exchange" should read --heat exchanger--.

Signed and Sealed this

Thirteenth Day of November, 2007

JON W. DUDAS
*Director of the United States Patent and Trademark Office*